United States Patent
Miyamoto et al.

(10) Patent No.: US 12,262,723 B2
(45) Date of Patent: Apr. 1, 2025

(54) FEED AND FOOD

(71) Applicant: Mitsubishi Chemical Corporation, Tokyo (JP)

(72) Inventors: Hirokuni Miyamoto, Ichikawa (JP); Motoaki Udagawa, Ichikawa (JP); Yosuke Takahashi, Tokyo (JP)

(73) Assignee: Mitsubishi Chemical Corporation, Tokyo (JP)

( * ) Notice: Subject to any disclaimer, the term of this patent is extended or adjusted under 35 U.S.C. 154(b) by 644 days.

(21) Appl. No.: 17/445,975

(22) Filed: Aug. 26, 2021

(65) Prior Publication Data

US 2021/0386094 A1  Dec. 16, 2021

Related U.S. Application Data

(63) Continuation of application No. PCT/JP2020/009720, filed on Mar. 6, 2020.

(30) Foreign Application Priority Data

Mar. 8, 2019  (JP) .................................. 2019-042569

(51) Int. Cl.
*A23K 10/18* (2016.01)
*A23K 50/75* (2016.01)
(Continued)

(52) U.S. Cl.
CPC .............. *A23K 10/18* (2016.05); *A23K 50/75* (2016.05); *A23L 13/00* (2016.08); *A23L 33/135* (2016.08);
(Continued)

(58) Field of Classification Search
None
See application file for complete search history.

(56) References Cited

U.S. PATENT DOCUMENTS

2017/0106027 A1*  4/2017  Tonda ................ A61K 31/7034
2021/0145898 A1*  5/2021  Kodama ............. A61K 35/742

FOREIGN PATENT DOCUMENTS

CN  106822522 A  6/2017
JP  2006-333842 A  12/2006
(Continued)

OTHER PUBLICATIONS

Endres, JR; et al; "Safety assessment of a proprietary preparation of a novel Probiotic, Bacillus coagulans, as a food ingredient" Food and Chemical Toxicology, 47, 1231-1238, 2009 (Year: 2009).*
(Continued)

*Primary Examiner* — David W Berke-Schlessel
(74) *Attorney, Agent, or Firm* — Oblon, McClelland, Maier & Neustadt, L.L.P.

(57) ABSTRACT

The present invention provides: a feed for reducing lipid peroxide or improving meat quality in a tissue in an edible portion of a domestic animal, the feed comprising a spore-bearing lactic acid bacterium and/or a spore-bearing thermophilic bacterium not corresponding to the spore-bearing lactic acid bacterium; and a food for reducing lipid peroxide in a human body, the food comprising a spore-bearing lactic acid bacterium and/or a spore-bearing thermophilic bacterium not corresponding to the spore-bearing lactic acid bacterium.

18 Claims, 4 Drawing Sheets

(51) Int. Cl.
| | |
|---|---|
| *A23L 13/00* | (2016.01) |
| *A23L 33/135* | (2016.01) |
| *A61K 9/00* | (2006.01) |
| *A61K 35/742* | (2015.01) |
| *A61P 3/12* | (2006.01) |

(52) U.S. Cl.
CPC .......... *A61K 9/0056* (2013.01); *A61K 35/742* (2013.01); *A61P 3/12* (2018.01); *A23V 2002/00* (2013.01)

(56) References Cited

FOREIGN PATENT DOCUMENTS

| | | | |
|---|---|---|---|
| JP | 2006-333845 A | 12/2006 | |
| JP | 2009-100728 A | 5/2009 | |
| JP | 2017-190298 A | 10/2017 | |
| JP | 2018-199642 A | 12/2018 | |
| JP | 7118344 B2 * | 8/2022 | ............. A61K 35/74 |

OTHER PUBLICATIONS

Mitsubishi-Chemical Foods Corporation; FDA granted a GRAS status for LACRIS[TM] (Bacillus coagulans SANK70258) in US; https://www.mfc.co.jp/en/news/pdf/20170911.pdf (Year: 2017).*

Nishida, Ayaka; et al; "*Bacillus hisashii* sp. nov., isolated from the caeca of gnotobiotic mice fed with thermophile-fermented compost" International Journal of Systematic and Evolutionary Microbiology, 65, 3944-3949, 20015 (Year: 2015).*

International Search Report issued Apr. 21, 2020 in PCT/JP2020/009720, 2 pages.

English translation of International Preliminary Report on Patentability and Written Opinion issued Sep. 23, 2021 in PCT/JP2020/009720, 8 pages.

Miyamoto Hirokuni et al., "Evaluation of the effect of oral administration of *Bacillus coagulans* on broiler meat quality", Japanese Journal Of Poultry Science, vol. 55 (issued for Spring Meeting), Mar. 2018, p. 22, lower col. with English Translation.

Japanese Office Action issued Aug. 20, 2024 in Japanese Patent Application No. 2020-038806 (with unedited, machine-generated English translation), 5 pages.

Inatomi T. et al., "Influence of Continuous Feeding of Probiotics on Senior Dogs," Journal of Pet Animal Nutrition, vol. 16, 2013, No. Suppl, pp. 50-51 (with partial English translation).

Office Action issued Mar. 5, 2024, in corresponding Japanese Patent Application No. 2020-038806 (with English Translation), 6 pages.

Reconsideration Report by Examiner before Appeal issued on Feb. 6, 2025, in corresponding Japanese Patent Application No. 2020-038806 (with machine translation).

* cited by examiner

FEED AND FOOD

CROSS REFERENCE TO RELATED APPLICATIONS

This application is a Continuation of PCT International Application No. PCT/JP2020/009720, filed on Mar. 6, 2020, which is claiming priority of Japanese Patent Application No. 2019-042569, filed on Mar. 8, 2019, the entire contents of which are incorporated herein by reference.

TECHNICAL FIELD

The present invention relates to a feed and a food for reducing lipid peroxide.

BACKGROUND ART

Conventionally, feeds have been practically used as nutrient sources in the fields of livestock industry and fisheries such as aquaculture, pig farming, and poultry farming. These feeds are demanded to have combinations of various functions such as a digestion-enhancing function, an odor-reducing function, an intestinal regulatory function, a calorie absorption regulatory function, a meat quality-improving function, an immune-enhancing function, a conception rate-enhancing function, and a feed-based water purification function.

In particular, in the recent livestock industry, agents such as antibiotics and antimicrobial agents are mixed in feeds to be given to livestock in order to increase the productivity by increasing the number of animals raised per unit area, from the viewpoint of preventing reduction of strength and resistance of livestock caused by stresses due to raising in overcrowded conditions. However, since appearance of resistant bacteria has become a worldwide problem, safe materials replacing these agents are demanded.

Patent Document 1 reports that feeding of livestock with a feed comprising as an effective component the spore-bearing lactic acid bacterium *Bacillus coagulans* (synonym: *Weizmannia coagulans*) results in suppression of the occurrence of diarrhea, and improvement of the intestinal flora (intestinal regulatory action), leading to improved health conditions of the livestock, and also results in an increase in the body weight at the time of shipping and a reduction of the feed conversion ratio, leading to promotion of the livestock growth.

Patent Document 2 proposes inclusion of thermophilic microorganisms in feeds, but the use of a group of unspecified microorganisms may be problematic from the viewpoint of reproducibility and stability of the effect.

PRIOR ART DOCUMENTS

Patent Documents

[Patent Document 1] JP 2006-333845 A
[Patent Document 2] JP 2009-100728 A

SUMMARY OF THE INVENTION

Problems to be Solved by the Invention

An object of the present invention is to provide a feed capable of reducing lipid peroxide in a tissue of an edible portion.

Means for Solving the Problems

In order to solve the above problem, the present inventors intensively studied to discover that, by mixing one or both of a spore-bearing lactic acid bacterium and a spore-bearing thermophilic bacterium in a feed, a meat quality-improving effect can be obtained due to reduction of lipid peroxide, thereby completing the present invention.

More specifically, the present invention is as follows.

[1] A feed for reducing lipid peroxide in a tissue in an edible portion of a domestic animal, the feed comprising one of a spore-bearing lactic acid bacterium and a spore-bearing thermophilic bacterium not corresponding to the spore-bearing lactic acid bacterium.

[2] A feed for reducing lipid peroxide in a tissue in an edible portion of a domestic animal, the feed comprising a spore-bearing lactic acid bacterium and a spore-bearing thermophilic bacterium not corresponding to the spore-bearing lactic acid bacterium.

[3] The feed according to [1] or [2], wherein the spore-bearing lactic acid bacterium is a bacterium belonging to the genus *Bacillus*.

[4] The feed according to any one of [1] to [3], wherein the spore-bearing lactic acid bacterium is *Bacillus coagulans*.

[5] The feed according to any one of [1] to [4], wherein the spore-bearing thermophilic bacterium is a bacterium belonging to the genus *Bacillus*.

[6] The feed according to any one of [1] to [5], wherein the spore-bearing thermophilic bacterium is *Bacillus hisashii*.

[7] The feed according to any one of [1] to [6], wherein the domestic animal is a domestic fowl.

[8] A method of reducing lipid peroxide in a tissue in an edible portion of a domestic animal, the method comprising the step of allowing the domestic animal to ingest a feed comprising one of a spore-bearing lactic acid bacterium and a spore-bearing thermophilic bacterium not corresponding to the spore-bearing lactic acid bacterium.

[9] A method of reducing lipid peroxide in a tissue in an edible portion of a domestic animal, the method comprising the step of allowing the domestic animal to ingest a feed comprising a spore-bearing lactic acid bacterium and a spore-bearing thermophilic bacterium not corresponding to the spore-bearing lactic acid bacterium.

[10] The method according to [8] or [9], wherein the spore-bearing lactic acid bacterium is a bacterium belonging to the genus *Bacillus*.

[11] The method according to any one of [8] to [10], wherein the spore-bearing lactic acid bacterium is *Bacillus coagulans*.

[12] The method according to any one of [8] to [11], wherein the spore-bearing thermophilic bacterium is a bacterium belonging to the genus *Bacillus*.

[13] The method according to any one of [8] to [12], wherein the spore-bearing thermophilic bacterium is *Bacillus hisashii*.

[14] The method according to any one of [8] to [13], wherein the domestic animal is a domestic fowl.

[15] A meat of a domestic animal raised on a feed comprising one of a spore-bearing lactic acid bacterium and a spore-bearing thermophilic bacterium not corresponding to the spore-bearing lactic acid bacterium.

[16] A meat of a domestic animal raised on a feed comprising a spore-bearing lactic acid bacterium and a spore-bearing thermophilic bacterium not corresponding to the spore-bearing lactic acid bacterium.

[17] A food for reducing lipid peroxide in a human body, the food comprising one of a spore-bearing lactic acid bacterium and a spore-bearing thermophilic bacterium not corresponding to the spore-bearing lactic acid bacterium.

[18] A food for reducing lipid peroxide in a human body, the food comprising a spore-bearing lactic acid bacterium and a spore-bearing thermophilic bacterium not corresponding to the spore-bearing lactic acid bacterium.

[19] The food according to [17] or [18], wherein the spore-bearing lactic acid bacterium is a bacterium belonging to the genus *Bacillus*.

[20] The food according to any one of [17] to [19], wherein the spore-bearing lactic acid bacterium is *Bacillus coagulans*.

[21] The food according to any one of [17] to [20], wherein the spore-bearing thermophilic bacterium is a bacterium belonging to the genus *Bacillus*.

[22] The food according to any one of [17] to [21], wherein the spore-bearing thermophilic bacterium is *Bacillus hisashii*.

[23] A method of reducing lipid peroxide in a human body, the method comprising the step of ingesting a food comprising one of a spore-bearing lactic acid bacterium and a spore-bearing thermophilic bacterium not corresponding to the spore-bearing lactic acid bacterium.

[24] A method of reducing lipid peroxide in a human body, the method comprising the step of ingesting a food comprising a spore-bearing lactic acid bacterium and a spore-bearing thermophilic bacterium not corresponding to the spore-bearing lactic acid bacterium.

[25] The method according to [23] or [24], wherein the spore-bearing lactic acid bacterium is a bacterium belonging to the genus *Bacillus*.

[26] The method according to any one of [23] to [25], wherein the spore-bearing lactic acid bacterium is *Bacillus coagulans*.

[27] The method according to any one of [23] to [26], wherein the spore-bearing thermophilic bacterium is a bacterium belonging to the genus *Bacillus*.

[28] The method according to any one of [23] to [27], wherein the spore-bearing thermophilic bacterium is *Bacillus hisashii*.

Effect of the Invention

According to the present invention, a meat quality-improving effect attributed to reduction of lipid peroxide can be obtained.

MODE FOR CARRYING OUT THE INVENTION

Figure 1:
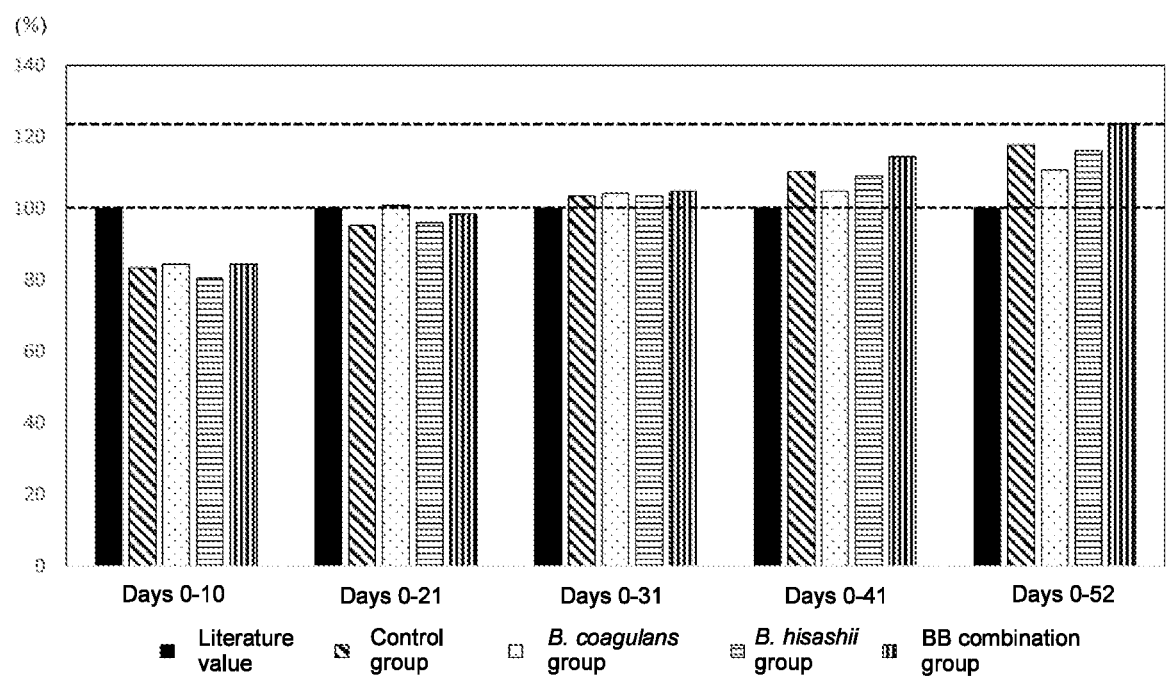
FIG. 1 is a graph for comparison of the feed conversion ratio among test groups of chicks on Day 0 to Day 52.

A first embodiment of the present invention is a feed comprising one or both of a spore-bearing lactic acid bacterium and a spore-bearing thermophilic bacterium not corresponding to the spore-bearing lactic acid bacterium (which may be hereinafter simply referred to as "spore-bearing thermophilic bacterium"). By allowing a domestic animal or an aquatic organism to ingest the feed according to the present embodiment, lipid peroxide in a tissue of an edible portion of the domestic animal or the aquatic organism can be reduced. Thus, by raising on the feed of the present embodiment, a domestic animal (meat) or an aquatic organism having improved meat quality can be provided.

Although the feed according to the present embodiment may comprise one or both of a spore-bearing lactic acid bacterium and a spore-bearing lactic acid bacterium, the feed preferably comprises both. This is because the inclusion of both a spore-bearing lactic acid bacterium and a spore-bearing lactic acid bacterium also produces effects such as prevention of diseases due to improvement of immunity or expression of biological defense factors, and growth promotion due to improvement of the feed conversion ratio.

A spore-bearing lactic acid bacterium is a lactic acid bacterium that forms spores, and highly resistant to dry conditions, heat, and acid. Even in cases where the bacterium is orally administered to a human, it reaches the intestine without being killed by gastric acid or bile, and then germinates, grows, and produces lactic acid in the intestine. Typical examples of a spore-bearing lactic acid bacterium include bacteria belonging to the genus *Bacillus* or the genus *Sporolactobacillus*. Among these, bacteria belonging to the genus *Bacillus* are preferred as the spore-bearing lactic acid bacterium. Specific examples of the bacteria belonging to the genus *Bacillus* include *Bacillus coagulans*. In the present embodiment, *Bacillus coagulans* is preferred as the spore-bearing lactic acid bacterium. Examples of *Bacillus coagulans* include the *Bacillus coagulans* SANK70258 strain, P-22 strain, lilac-01 strain, SIM-7 DSM14043 strain, C101 strain, NBRC12583 strain, GBI-1 strain, GBI-20 strain, GBI-30 strain, and GBI-40 strain. The *Bacillus coagulans* SANK70258 strain is especially preferred from the viewpoint of stable supply and availability.

As the spore-bearing lactic acid bacterium, a commercially available spore-bearing lactic acid bacterium (for example, "LACRIS-S", "LACRIS-S granule", and "LACRIS-10 for feed", manufactured by Mitsubishi-Chemical Foods Corporation; "Ganeden BC30", manufactured by Ganeden Inc.; "Lactospore", manufactured by SABINSA; "BC30", manufactured by Kerry; "Lilac lactic acid bacteria", manufactured by Arterio-Bio Co., Ltd.; "Unique IS2", manufactured by UNIQUEBIOTECH; or "Caliter", manufactured by Asahi Calpis Wellness Co., Ltd.) may be used. When appropriate, this may be used after culture in an appropriate medium. In the present embodiment, this may be used either in the state of spores or in the state of a mixture of spores and vegetative cells, in the form of a powder, granules, or a liquid. In some cases, the spore-bearing lactic acid bacterium in the present embodiment may be dead bacterial cells prepared by heat drying.

In cases where the feed comprises a spore-bearing lactic acid bacterium, its content is usually not less than $1.0 \times 10^4$ cfu/g, preferably not less than $3.0 \times 10^4$ cfu/g, more preferably not less than $5.0 \times 10^4$ cfu/g, still more preferably not less than $8.0 \times 10^4$ cfu/g, especially preferably not less than $1.0 \times 10^5$ cfu/g, and is usually not more than $1.0 \times 10^{12}$ cfu/g, preferably not more than $1.0 \times 10^{10}$ cfu/g, more preferably not more than $5.0 \times 10^6$ cfu/g, still more preferably not more than $1.0 \times 10^6$ cfu/g, especially preferably not more than $3.0 \times 10^5$ cfu/g. In cases where the content of the spore-bearing lactic acid bacterium is within the above described ranges, there are advantages from the viewpoint of the cost, from the viewpoint of improving uniformity during mixing with a feed, and from the viewpoint of easily obtaining a growth promotion effect in a mode in which the feed comprises both a spore-bearing lactic acid bacterium and a spore-bearing thermophilic bacterium.

The spore-bearing thermophilic bacterium is a microorganism having an optimal growth temperature of not less than 40° C. Specific examples of the spore-bearing thermophilic bacterium include thermophilic microorganisms belonging to the genus *Bacillus, Oceanobacillus, Paenibacillus, Anoxybacillus,* or *Lysinibacillus.* Other examples of the spore-bearing thermophilic bacterium include thermophilic microorganisms belonging to the genus *Methanopyrus, Geogemma, Pyrolobus, Pyrodictium, Hyperthermus, Pyrococcus, Pyrobaculum, Thermococcus, Aeropyrum, Aquifex, Thermotoga, Thermodesulfobacterium, Thermus, Geobacillus, Thermomyces,* or *Clostridium.* Among these, bacteria belonging to the genus *Bacillus* are preferred. Examples of the bacteria belonging to the genus *Bacillus* include *Bacillus thermoamylovorans* and *Bacillus thermocloacae.* More specific examples of the bacteria include *Bacillus hisashii,* which is a closely related species of *Bacillus thermoamylovorans*; a species closely related to *Bacillus thermocloacae* belonging to the bacterial phylum Firmicutes (deposited in the GenBank database as no. AB298562); and a species closely related to *Bacillus thermoamylovorans* (deposited in the database as no. AB298559). *Bacillus hisashii,* which is a closely related species of *Bacillus thermoamylovorans,* is preferred. As the *Bacillus hisashii,* BP-863 (N-11) is preferred. The thermophilic bacterium *Bacillus hisashii* BP-863 has been deposited with Patent Microorganisms Depositary, National Institute of Technology and Evaluation (address: Room 122, 2-5-8 Kazusakamatari, Kisarazu-shi, Chiba) as of Jan. 15, 2010 as an international deposit (accession number: NITE BP-863). The spore-bearing thermophilic bacterium may be dead bacterial cells prepared by heat drying. The spore-bearing thermophilic bacterium may be complex bacteria, such as a thermophilic inoculum PTA-1773 or thermophilic complex bacteria BP-1051. The thermophilic inoculum PTA-1773 has been deposited with ATCC (American Type Culture Collection, 10801 University Boulevard Manassas, Virginia 20110-2209 U.S.A.) as of May 1, 2000 as an international deposit (accession number: PTA-1773). The thermophilic complex bacteria BP-1051 has been deposited with Patent Microorganisms Depositary, National Institute of Technology and Evaluation (address: Room 122, 2-5-8 Kazusakamatari, Kisarazu-shi, Chiba) as of Jan. 18, 2011 as an international deposit (accession number: NITE BP-1051).

In cases where the feed comprises a spore-bearing thermophilic bacterium, its content is usually not less than $1.0 \times 10$ cfu/g, preferably not less than $1.0 \times 10^2$ cfu/g, more preferably not less than $1.0 \times 10^3$ cfu/g, still more preferably not less than $1.0 \times 10^4$ cfu/g, especially preferably not less than $5.0 \times 10^4$ cfu/g, and is usually not more than $1.0 \times 10^{12}$ cfu/g, preferably not more than $1.0 \times 10^{10}$ cfu/g, more preferably not more than $1.0 \times 10^8$ cfu/g, still more preferably not more than $1.0 \times 10^6$ cfu/g, especially preferably not more than $5.0 \times 10^5$ cfu/g. In cases where the content of the spore-bearing thermophilic bacterium is within the above described ranges, there are advantages from the viewpoint of obtaining an effect that reduces fat accumulation, and from the viewpoint of easily obtaining a growth promotion effect in a mode in which the feed comprises both a spore-bearing lactic acid bacterium and a spore-bearing thermophilic bacterium.

In cases where the feed comprises both a spore-bearing lactic acid bacterium and a spore-bearing thermophilic bacterium, the mixing ratio between the spore-bearing lactic acid bacterium and the spore-bearing thermophilic bacterium, in terms of their numbers, is usually not less than 1:1, preferably not less than 2:1, more preferably not less than 3:1, still more preferably not less than 5:1, and is usually not more than 1,000,000:1, preferably not more than 500,000:1, more preferably not more than 100,000:1, still more preferably not more than 50,000:1. Within the above ranges, the effect of the present invention produced by the combined use of a spore-bearing lactic acid bacterium and a spore-bearing thermophilic bacterium can be easily obtained, which is preferred.

The feed herein is not limited as long as it is given to a domestic animal for raising it. The feed includes feeds in a solid form, feeds in a liquid form, and water.

Mannose, mannooligosaccharides, and the like for the purpose of aiding the action of live bacteria; and other oligosaccharides, organic acids, water-soluble dietary fibers, starch, insoluble dietary fibers, and the like as prebiotics; may be added to the feed. Further, when necessary, the feed may contain a stabilizer or an excipient. Examples of the stabilizer include silicic anhydride. Examples of the excipient include cereals such as corn, wheat, soybean, and milo; sugars such as lactose, sucrose, and glucose; vegetable oil meals such as soybean meal, corn gluten meal, sesame oil meal, corn germ meal, rapeseed oil meal, and distillers grains; chaffs and brans such as bran, rice bran, defatted rice bran, and corn gluten feeds; animal materials such as fish flour; vegetable oils such as palm oil, lard, and corn oil; starches such as corn starch and potato starch; minerals such as calcium carbonate; vitamins such as vitamin E; dextrin; corn steep liquor; paprika extracts; and alfalfa meal.

In the present description, "prevention of diseases" means a state where an animal including human or an aquatic organism has improved immunity, so that the animal or the aquatic organism is less likely to develop the diseases. The prevention of diseases can be judged based on improvement of expression of biological defense factors.

The "meat quality improvement" in the present description means reduction of lipid peroxide in a tissue in an edible portion of a domestic animal or an aquatic organism. Lipid peroxide derived from neutral fat is said to generate superoxide anion in cells, and the superoxide anion has an action that causes damage to DNA in the nucleus. Thus, the lipid peroxide is thought to be one of the large number of causes of carcinogenesis, and to be involved in aging and lifestyle-related diseases. Final products of lipid peroxidation may have mutagenicity and carcinogenicity. For example, the final product malondialdehyde generates a DNA adduct by reaction with deoxyadenosine or deoxyguanosine in DNA.

Thus, from the viewpoint of maintenance of quality and freshness of meat, suppression of the content of final lipid peroxidation products represented by malondialdehyde in an edible portion of a domestic animal or an aquatic organism to a low value is a very important approach. For example, TBARS measurement, which is often used as an index related to meat quality, is known as an index reflecting the content of malondialdehyde.

"Reduction of lipid peroxide in a tissue in an edible portion of a domestic animal or an aquatic organism" as the effect of the feed according to the present embodiment means that the amount of lipid peroxide per tissue weight of an edible portion of a domestic animal or an aquatic organism is smaller in a case where the domestic animal or the aquatic organism is allowed to ingest the feed according to the present embodiment than in a case where the domestic animal or the aquatic organism is not allowed to ingest the feed (for example, in a case where the domestic animal or the aquatic organism is allowed to ingest the feed which is the same as the feed according to the present embodiment except that the spore-bearing lactic acid bacterium and the spore-bearing thermophilic bacterium are excluded).

The feed according to the present embodiment may be given to a domestic animal or an aquatic organism. A commercially available feed may be used as the feed to which the spore-bearing lactic acid bacterium and the spore-bearing thermophilic bacterium are to be added. Examples of the domestic animal include cows, horses, pigs, sheep, goats, and domestic fowls. Domestic fowls are preferred. Examples of the domestic fowls include chickens (such as broilers, laying hens, and locally produced chickens, preferably broilers), gooses, mallards, domestic ducks (aigamo), ducks, quails, turkeys, and pheasants. Examples of the aquatic organism include fish, amphibians, and aquatic mammals that can be reared. Examples of the fish include flounder, sardine, tuna, mackerel, salmon, bonito, herring, saury, horse mackerel, cod, Japanese amberjack (buri), Japanese amberjack (hamachi), sea bream, greater amberjack (kanpachi), yellowtail amberjack (hiramasa), threadsail filefish, eel, rainbow trout, trout, pufferfish, grass carp, silver carp, carp, tilapia, and bighead carp.

The amount of the feed given to the domestic animal or the aquatic organism is not limited, and may be appropriately set depending on, for example, the type and the age in days of the domestic animal or the aquatic organism. The number of times and the number of days of allowing the domestic animal or the aquatic organism to ingest the feed may also be appropriately set depending on, for example, the type and the age in days of the domestic animal or the aquatic organism. For example, the domestic animal or the aquatic organism may be allowed to ingest the feed at least once per day, preferably 1 to 5 times per day, continuously for not less than 2 days, preferably not less than 10 days, more preferably not less than 30 days.

A second embodiment of the present invention is a food comprising one or both of a spore-bearing lactic acid bacterium and a spore-bearing thermophilic bacterium not corresponding to the spore-bearing lactic acid bacterium. By ingestion of the food, lipid peroxide in a human body can be reduced.

The lipid peroxide in a human body is not limited, and may be, for example, lipid peroxide in a tissue of muscle or an organ, or may be lipid peroxide in blood.

Although the food according to the present embodiment may comprise one or both of a spore-bearing lactic acid bacterium and a spore-bearing lactic acid bacterium, the feed preferably comprises both. This is because the inclusion of both a spore-bearing lactic acid bacterium and a spore-bearing lactic acid bacterium in the food also has effects such as prevention of diseases due to improvement of immunity or expression of biological defense factors.

The description on the spore-bearing lactic acid bacterium and the spore-bearing thermophilic bacterium not corresponding to the spore-bearing lactic acid bacterium as components of the feed according to the first embodiment is applied to the spore-bearing lactic acid bacterium and the spore-bearing thermophilic bacterium not corresponding to the spore-bearing lactic acid bacterium as components of the food according to the present embodiment.

In cases where the food comprises a spore-bearing lactic acid bacterium, its content is usually $1.0\times10^4$ cfu/g or more and $1.0\times10^9$ cfu/g or less, preferably $1.0\times10^5$ cfu/g or more and $1.0\times10^8$ cfu/g or less.

In cases where the food comprises a spore-bearing thermophilic bacterium, its content is usually $1.0\times10^4$ cfu/g or more and $1.0\times10^9$ cfu/g or less, preferably $1.0\times10^5$ cfu/g or more and $1.0\times10^8$ cfu/g or less.

In cases where the food comprises both a spore-bearing lactic acid bacterium and a spore-bearing thermophilic bacterium, the mixing ratio between the spore-bearing lactic acid bacterium and the spore-bearing thermophilic bacterium, in terms of their numbers, is usually 1:1 or more and 100,000:1 or less, preferably 2:1 or more and 10,000:1 or less.

The amount of the spore-bearing lactic acid bacterium to be ingested per day is usually $1.0\times10^7$ cfu/day or more and $2.0\times10^9$ cfu/day or less, preferably $5.0\times10^7$ cfu/day or more and $2.0\times10^8$ cfu/day or less, respectively. The amount to be ingested per day may be ingested at once or dividedly in two or more times.

The amount of the spore-bearing thermophilic bacterium to be ingested per day is usually $1.0\times10^4$ cfu/day or more and $2.0\times10^9$ cfu/day or less, preferably $5.0\times10^5$ cfu/day or more and $2.0\times10^6$ cfu/day or less, respectively. The amount to be ingested per day may be ingested at once or dividedly in two or more times.

EXAMPLES

The present invention is described below more concretely by way of Examples. However, the present invention is not limited to the following Examples.

The chicken strain Chunky was used as a test subject. The tests in Examples 1 to 3 and Comparative Example 1 were carried out for the groups divided based on the feed as shown in Table 1. During the young chick period, that is, until Day 10 after hatching of the test subject, the chicks were raised in battery cages. From the middle chick period to the late chick period, that is, from Day 11 to Day 52 after hatching of the test subject, the chicks were raised by floor feeding.

TABLE 1

| Test group | Days 0 to 10 (young chick period) Battery-raising period | Days 11 to 52 (from middle chick period to late chick period) Floor-feeding period |
|---|---|---|
| Comparative Exmple 1 Control group | — | — |
| Example 1 BB combination group (Combined use of B. coagulans + B. Hisashii) | Addition to drinking water B. coagulans 0.01% by mass B. hisashii 0.01% by mass | Addition to a commercially available feed B. coagulans 0.01% by mass B. hisashii 0.01% by mass |
| Example 2 Bacillus coagulans group (LACRIS-10) | Addition to drinking water 0.01% by mass | Addition to a commercially available feed 0.01% by mass |

TABLE 1-continued

| Test group | Days 0 to 10 (young chick period) Battery-raising period | Days 11 to 52 (from middle chick period to late chick period) Floor-feeding period |
|---|---|---|
| Example 3 *Bacillus hisashii* group (BP-863) | Addition to drinking water 0.01% by mass | Addition to a commercially available feed 0.01% by mass |

Example 1

The spore-bearing lactic acid bacterium "LACRIS-10" (manufactured by Mitsubishi-Chemical Foods Corporation; *Bacillus coagulans*, not less than $1.0 \times 10^9$ cfu/g) and the spore-bearing thermophilic bacterium "BP-863" (manufactured by Sermas Co., Ltd.; *Bacillus hisashii*, not less than $1.0 \times 10^5$ cfu/g), which are mixtures prepared by mixing starch (manufactured by Matsutani Chemical Industry Co., Ltd.) as an excipient and bacterial cells together, were used. Each of "LACRIS-10" and "BP-863" was added to drinking water or a commercially available feed to an amount corresponding to 0.01% by mass such that the drinking water for the chicks on Days 0 to 10 and the commercially available feed for the chicks on Day 11 and thereafter contained the spore-bearing lactic acid bacterium at not less than $10^5$ cfu/g and the spore-bearing thermophilic bacterium at not less than $1.0 \times 10$ cfu/g as a result. As the commercially available feed, ("Marugun Chicken Foods", manufactured by Kumiai Haigo Shiryo) was used.

Example 2

The drinking water and the feed for the chicks were prepared in the same manner as in Example 1 except that only the spore-bearing lactic acid bacterium was added as the bacterial species instead of adding the spore-bearing lactic acid bacterium and the spore-bearing thermophilic bacterium.

Example 3

The drinking water and the feed for the chicks were prepared in the same manner as in Example 1 except that only the spore-bearing thermophilic bacterium was added as the bacterial species instead of adding the spore-bearing lactic acid bacterium and the spore-bearing thermophilic bacterium.

Comparative Example 1

In a control group, sterile water was added to the drinking water for the chicks on Days 0 to 10 at 0.01% by mass, and starch as an excipient was added to the commercially available feed ("Marugun Chicken Foods", manufactured by Kumiai Haigo Shiryo) for Day 11 and thereafter to an amount corresponding to 0.01% by mass.

Test Example 1

The feed conversion ratios of the chicks on Days 0 to 52 in the test groups of Examples 1 to 3 and Comparative Example 1 were calculated with respect to values according to a literature ("Chunky broiler performance objectives 2014", Aviagen, Nippon Chunky Co., Ltd.; unsexed performance), which was taken as 100%. The results are shown in FIG. 1. In the early chick period, the feed conversion ratio tended to be lower than the value according to the literature. However, the feed conversion ratio was gradually improved, and remarkable improvement was observed at 41 days old and 52 days old in the BB combination group.

Test Example 2

Figure 2:
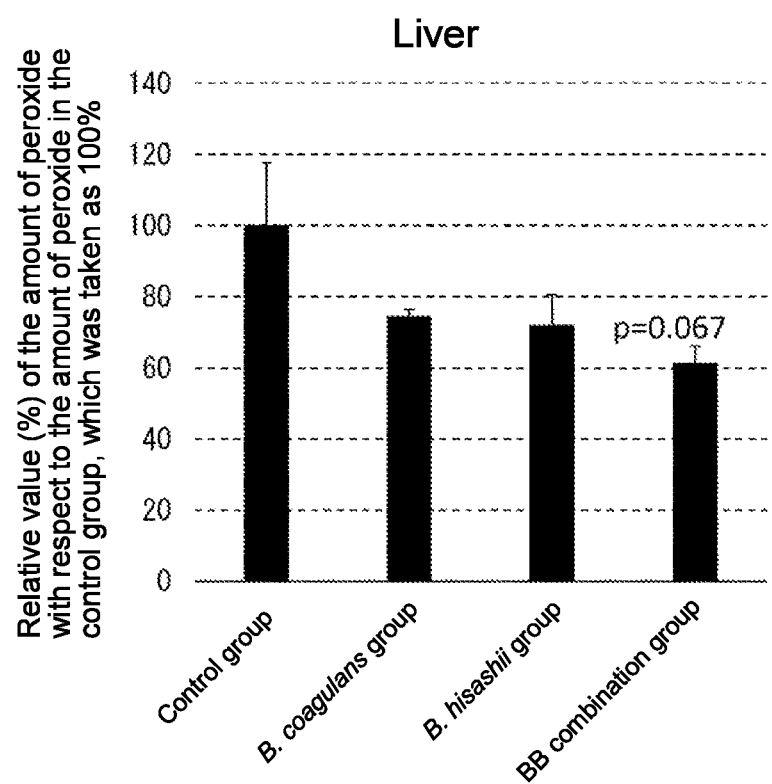
FIG. 2 is a graph for comparison of the ratio of peroxide in the liver tissue among test groups of chickens.

The amounts of peroxide (in terms of malondialdehyde) per tissue weight in the livers of the chickens in the test groups of Examples 1 to 3 and Comparative Example 1 were measured according to a conventional method. FIG. 2 shows the results of calculation of the measured values in the test groups of Examples 1 to 3, expressed as relative values with respect to the measured value in Comparative Example 1 (control group), which was taken as 100%. According to FIG. 2, the *B. coagulans* group, the *B. hisashii* group, and the BB combination group in which *B. coagulans* and *B. hisashii* were used in combination showed decreased ratios of peroxide per tissue weight in the liver compared to the control group. Among these, the BB combination group showed the lowest value of the ratio of peroxide. It can be seen that a meat quality-improving effect can be obtained by inclusion of *B. coagulans* or *B. hisashii* in the feed, and that a synergistic effect on meat quality improvement can be obtained by inclusion of both *B. coagulans* and *B. hisashii*.

Test Example 3

Figure 3:
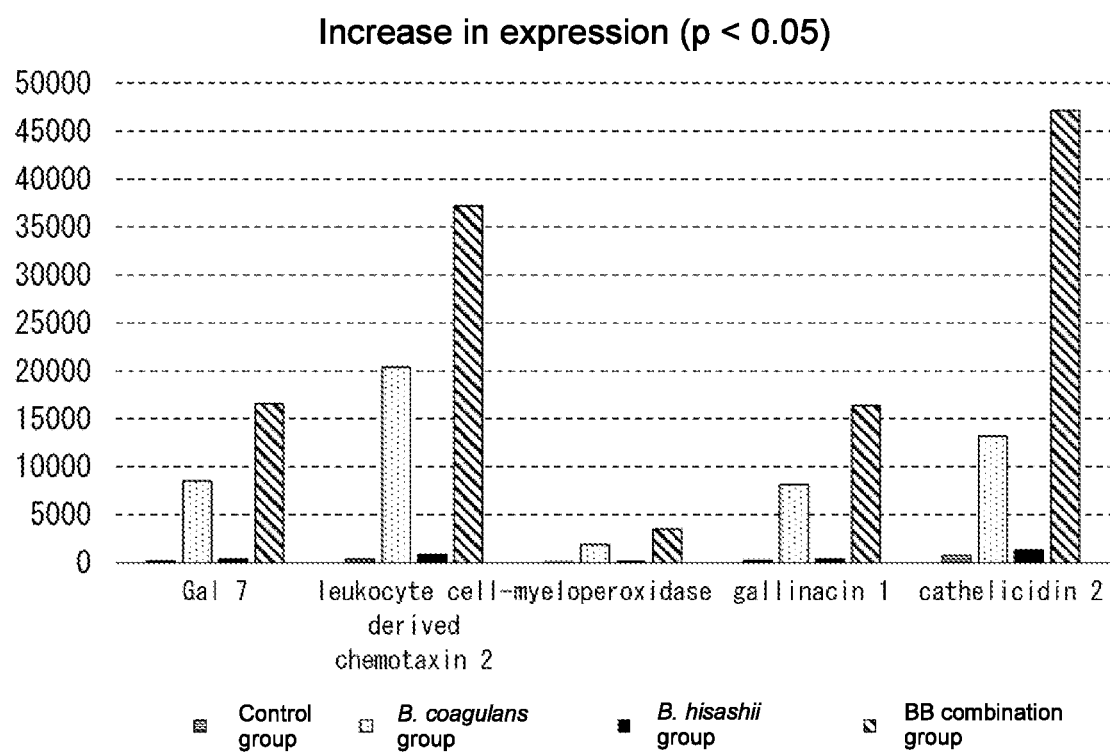
FIG. 3 is a graph for comparison of the expression levels of biological defense factors in the liver tissue among test groups of chickens.
Figure 4:
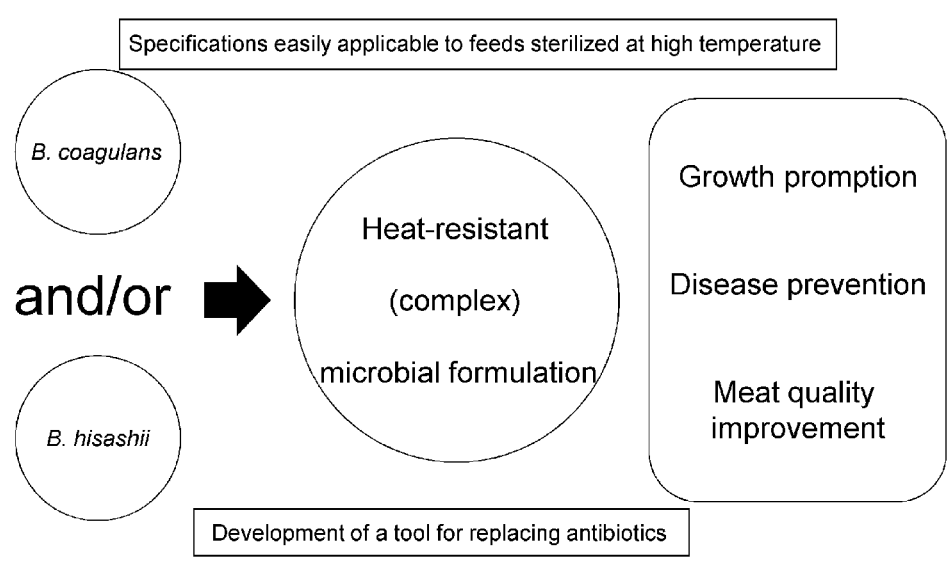
FIG. 4 is a schematic diagram of the present invention.

Expression, in the liver tissue, of genes (Gal 7, leukocyte cell-derived chemotaxis 2, myeloperoxidase, galloinacin, and cathelicidin) that contribute to improvement of immunity was investigated for the test groups of Examples 1 to 3 and Comparative Example 1. The p-value (significance probability) was set to 0.05. The results are shown in FIG. 3. The *B. hisashii* group showed only low levels of expression of the genes involved in improvement of immunity. In contrast, the *B. coagulans* group showed expression of the genes, and the BB combination group in which *B. coagulans* and *B. hisashii* were used in combination showed much higher expression levels of the genes than those in the *B. coagulans* group. It can be seen that a synergistic effect on improvement of immunity can be obtained by inclusion of both *B. coagulans* and *B. hisashii* in the feed.

What is claimed is:

1. A feed for reducing lipid peroxide in a tissue in an edible portion of a domestic animal, the feed comprising a spore-bearing lactic acid bacterium and a spore-bearing thermophilic bacterium not corresponding to the spore-bearing lactic acid bacterium,
wherein
the spore-bearing lactic acid bacterium is *Bacillus coagulans*, and
the spore-bearing thermophilic bacterium is *Bacillus hisashii*.

2. The feed according to claim 1, wherein the domestic animal is a domestic fowl.

3. A method of reducing lipid peroxide in a tissue in an edible portion of a domestic animal, the method comprising:
allowing the domestic animal to ingest a feed comprising a spore-bearing lactic acid bacterium and a spore-bearing thermophilic bacterium not corresponding to the spore-bearing lactic acid bacterium,
wherein
the spore-bearing lactic acid bacterium is *Bacillus coagulans*, and
the spore-bearing thermophilic bacterium is *Bacillus hisashii*.

4. The method according to claim 3, wherein the domestic animal is a domestic fowl.

5. A food for reducing lipid peroxide in a human body, the food comprising a spore-bearing lactic acid bacterium and a spore-bearing thermophilic bacterium not corresponding to the spore-bearing lactic acid bacterium,
wherein
the spore-bearing lactic acid bacterium is *Bacillus coagulans*, and
the spore-bearing thermophilic bacterium is *Bacillus hisashii*.

6. A method of reducing lipid peroxide in a human body, the method comprising: ingesting a food comprising a spore-bearing lactic acid bacterium and a spore-bearing thermophilic bacterium not corresponding to the spore-bearing lactic acid bacterium,
wherein
the spore-bearing lactic acid bacterium is *Bacillus coagulans*, and
the spore-bearing thermophilic bacterium is *Bacillus hisashii*.

7. The feed according to claim 1, wherein a content of the spore-bearing lactic acid bacterium is from $5.0 \times 10^6$ cfu/g to $1.0 \times 10^{12}$ cfu/g.

8. The feed according to claim 1, wherein a content of the spore-bearing thermophilic bacterium is from $1.0 \times 10$ cfu/g to $1.0 \times 10^6$ cfu/g.

9. The method according to claim 3, wherein a content of the spore-bearing lactic acid bacterium in the feed is from $5.0 \times 10^6$ cfu/g to $1.0 \times 10^{12}$ cfu/g.

10. The method according to claim 3, wherein a content of the spore-bearing thermophilic bacterium in the feed is from $1.0 \times 10$ cfu/g to $1.0 \times 10^6$ cfu/g.

11. The food according to claim 5, wherein a content of the spore-bearing lactic acid bacterium is from $5.0 \times 10^6$ cfu/g to $1.0 \times 10^{12}$ cfu/g.

12. The food according to claim 5, wherein a content of the spore-bearing thermophilic bacterium is from $1.0 \times 10$ cfu/g to $1.0 \times 10^6$ cfu/g.

13. The method according to claim 6, wherein a content of the spore-bearing lactic acid bacterium in the food is from $5.0 \times 10^6$ cfu/g to $1.0 \times 10^{12}$ cfu/g.

14. The method according to claim 6, wherein a content of the spore-bearing thermophilic bacterium in the food is from $1.0 \times 10$ cfu/g to $1.0 \times 10^6$ cfu/g.

15. The feed according to claim 1, wherein a mixing ratio of the spore-bearing lactic acid bacterium and the spore-bearing thermophilic bacterium, in terms of their numbers, is from 1:1 to 1,000,000:1.

16. The method according to claim 3, wherein a mixing ratio of the spore-bearing lactic acid bacterium and the spore-bearing thermophilic bacterium, in terms of their numbers, is from 1:1 to 1,000,000:1.

17. The food according to claim 5, wherein a mixing ratio of the spore-bearing lactic acid bacterium and the spore-bearing thermophilic bacterium, in terms of their numbers, is from 1:1 to 1,000,000:1.

18. The method according to claim 6, wherein a mixing ratio of the spore-bearing lactic acid bacterium and the spore-bearing thermophilic bacterium, in terms of their numbers, is from 1:1 to 1,000,000:1.

* * * * *